United States Patent [19]

Venugopal

[11] Patent Number: 5,650,517
[45] Date of Patent: Jul. 22, 1997

[54] PROCESS FOR THE PREPARATION OF 2,3-DIFLUORO-5-HALOPYRIDINES

[75] Inventor: Balakrishnan Venugopal, Baton Rouge, La.

[73] Assignee: Ciba-Geigy Corporation, Ardsley, N.Y.

[21] Appl. No.: 333,103

[22] Filed: Nov. 1, 1994

[51] Int. Cl.⁶ .................................................. C07D 213/61
[52] U.S. Cl. .................................................. 546/345
[58] Field of Search .................................................. 546/345

[56] References Cited

U.S. PATENT DOCUMENTS

| | | | |
|---|---|---|---|
| 4,031,100 | 6/1977 | Giacobbe | 546/345 |
| 4,071,521 | 1/1978 | Muench | 546/345 |
| 4,565,568 | 1/1986 | Johnston et al. | 504/258 |
| 4,713,109 | 12/1987 | Schurter et al. | 504/258 |
| 4,822,887 | 4/1989 | Little | 546/345 |

FOREIGN PATENT DOCUMENTS

| | | |
|---|---|---|
| 0097460 | 1/1984 | European Pat. Off. . |
| 0146924 | 7/1985 | European Pat. Off. . |
| 0270221 | 6/1988 | European Pat. Off. . |
| 0248968 | 12/1989 | European Pat. Off. . |
| 0556737 | 8/1993 | European Pat. Off. . |

OTHER PUBLICATIONS

Patent Abstracts of Japan, vol. 95 No. 1, 28, 1995 of JP-A-06-298734 (1994).
G. C. Finger et al., J. Organ. Chem., vol. 28, pp. 1666–1668 (1963).

*Primary Examiner*—C. Warren Ivy
*Assistant Examiner*—D. Margaret M. Mach
*Attorney, Agent, or Firm*—Edward McC. Roberts; Kevin T. Mansfield; Gabriel Lopez

[57] ABSTRACT

2,3-Difluoro-5-halopyridines of the formula I

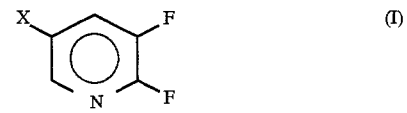

wherein X is Cl or Br are prepared by a process which comprises reacting a starting 2,3,5-trihalopyridine of the formula II

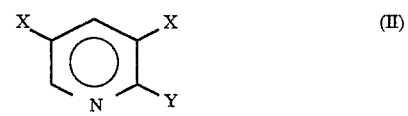

wherein each X is individually Br or Cl and Y is F, Cl or Br with an effective amount of potassium fluoride in the presence of a mixture of sulfolane and a tetralkylurea and/or a dialkyl-alkyleneurea as diluent, at an effective temperature up to the boiling point of the diluent, optionally in the presence of a phase-transfer catalyst such as a crown ether or polyglycol ether. The compounds are useful as intermediates to prepare herbicides.

20 Claims, No Drawings

PROCESS FOR THE PREPARATION OF 2,3-DIFLUORO-5-HALOPYRIDINES

The present invention relates to an improved process for the preparation of 5-chloro-2,3-difluoropyridine or 5-bromo-2,3-difluoropyridine using potassium fluoride as the fluorinating agent.

Certain 2,3-difluoro-5-halopyridines have been known for some time. See, for example Abromovitch, "Pyridine and its Derivatives", Supplement Part Two, page 439 and Coe et al., J. Fluorine Chem., 21 (1982), 171–189.

U.S. Pat. No. 3,798,228 to Boudakian et al. teaches that difluoropyridines and substituted difluoropyridines can be prepared via diazotization of a diaminopyridine such as 5-bromo-2,3-diaminopyridine in hydrogen fluoride with the simultaneous displacement of both amino groups, i.e. a double Schiemann reaction. It also teaches that the resulting difluoropyridines are useful per se as preemergent herbicides.

2,3-Difluoro-5-halopyridines of the formula I

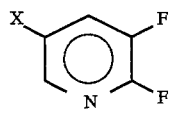

wherein X is Cl or Br are also useful as intermediates for the preparation of herbicidal 2-(4-((3-fluoro-5-chloro- or -bromo-2-pyridyl)oxy)phenoxy)propionic acid derivatives such as those disclosed in U.S. Pat. Nos. 4,505,743, 4,713,109 and 4,935,051 to Schurter et al. and 4,565,568, to Johnston et al. The latter patent teaches to prepare 5-chloro-2,3-difluoropyridine and 5-bromo-2,3-difluoropyridine by reaction of 2,3,5-trichloropyridine or 2,3,5-tribromopyridine, respectively, with cesium fluoride in DMSO or sulfolane. DE-A-3700779 teaches to prepare 5-chloro-2,3-difluoropyridine by reaction of 2,5-dichloro-3-nitropyridine with cesium fluoride in sulfolane.

It is known from U.S. Pat. Nos. 4,031,100 and 4,071,521 that 2,6-difluoropyridine can be readily prepared by reaction of 2,6-dichloropyridine with more economical potassium fluoride in DMSO. However, replacement of a chlorine or bromine in the 3-position by fluorine using potassium fluoride is much more difficult. Thus, Finger et al., J. Org. Chem. 28, 1666 (1963), discloses that reaction of 2,3,5-trichloropyridine with 2 moles of potassium fluoride in dimethyl sulfone for 24 hours at 200° C. gives only 2-fluoro-3,4-dichloropyridine, i.e. no exchange occurred at the 3-position.

U.S. Pat. No. 4,822,887 (Little et al.) teaches and claims a process for the preparation of a 2,3-difluoro-5-halopyridine of the formula

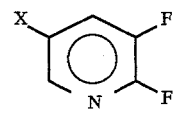

wherein X is Cl or Br, which comprises reacting a starting compound having the formula

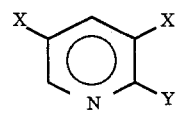

wherein each X is individually Br or Cl and Y is F, Cl or Br with an effective amount of potassium fluoride in a polar aprotic diluent at an effective temperature of from 50° C. to the boiling point of the diluent, optionally in the presence of a phase-transfer catalyst, removing the product compound by distillation essentially as it is formed, and, optionally, adding additional starting compound as the product compound is removed. Suitable diluents include DMSO, DMF, dimethylacetamide, diethylacetamide, MIBK, HMPA, sulfolane and NMP, with NMP, DMSO and sulfolane being preferred.

Removing the product essentially as it is formed by distillation is taught to be essential to replace a 3-Cl or 3-Br moiety by F in the above compounds when using potassium fluoride as the fluorinating agent. However, continuous fractional distillation is very energy intensive. It is therefore an object of this invention to provide a process for the preparation of a 2,3-difluoro-5-halopyridine of the formula I

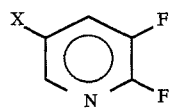

wherein X is Cl or Br by reacting a starting 2,3,5-trihalopyridine of the formula II

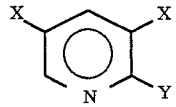

wherein each X is individually Br or Cl and Y is F, Cl or Br with an effective amount of potassium fluoride in a polar aprotic diluent at an effective temperature, optionally in the presence of a phase-transfer catalyst, with a high conversion of the starting compound to di-and trifluoro products in a reasonable time and without the necessity to remove the product by distillation essentially as it is formed. Surprisingly, this object can be accomplished if the reaction is carried out in a mixture of sulfolane and a tetralkylurea and/or a dialkyl-alkyleneurea as diluent in place of the diluents employed in the past. Thus the present invention comprises a process for the preparation of a 2,3-difluoro-5-halopyridine of the formula I

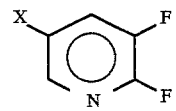

wherein X is Cl or Br which comprises reacting a starting 2,3,5-trihalopyridine of the formula II

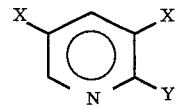

wherein each X is individually Br or Cl and Y is F, Cl or Br with an effective amount of potassium fluoride in a polar aprotic diluent comprising a mixture of sulfolane and a tetralkylurea and/or a dialkyl-alkyleneurea, at an effective temperature of from 150° C. up to the boiling point of the diluent, optionally in the presence of a phase-transfer catalyst.

When Y is Cl or Br, the process produces a mixture of the corresponding 3,5-dihalo-2-fluoro- and 5-halo-2,3-difluoropyridines, from which the more volatile compound of formula I can be separated by distillation.

Preferably 2,3,5-trichloropyridine and/or 3,5-dichloro-2-fluoropyridine is used to prepare the compound of formula I where X is Cl, 5-chloro-2,3-difluoropyridine.

The tetralkylureas useful in the present invention are preferably tetra-substituted by $C_1$–$C_4$ alkyl groups, especially methyl or ethyl groups. Tetramethylurea is especially preferred.

Dialkyl-alkyleneureas include both N,N-di($C_1$–$C_2$alkyl)-N'-$C_4$–$C_5$alkyleneureas and N,N'-di($C_1$–$C_2$alkyl)-N,N'-propyleneureas. Most especially preferred is N,N'-dimethylpropyleneurea. These tetralkylurea and/or dialkyl-alkyleneureas are commercially available or can be made by known methods.

The amount of tetralkylurea and/or dialkyl-alkyleneurea in the diluent mixture can vary from 5 to 95 % by weight. Preferably it comprises 5 to 30 % by weight of the mixture.

The amount of diluent to employ is not critical but should be sufficient to maintain good mixing. Use of about 3–8 parts of diluent by weight, especially 4–6 parts of diluent per part of starting 2,3,5-trihalopyridine of the formula II is preferred.

While the reaction mixture is preferably substantially anhydrous, the small amounts of water normally present in the diluents usually have little effect on the reaction. If desired, water can be removed from the diluent mixture before adding the starting compound of the formula II by distillation, optionally under vacuum, of a small amount of said diluent mixture. Alternatively, a small amount such as 5–10% by weight based on the diluent mixture of a hydrocarbon such as toluene or xylene can be added to facilitate azeotropic drying. The potassium fluoride is also advantageously present during the drying.

An effective amount of preferably substantially anhydrous and finely divided potassium fluoride, such as commercially available spray dried 99% potassium fluoride, is employed as the fluorinating agent. By an effective amount is meant at least one mole of potassium fluoride per Cl or Br in the 2- and/or 3-position of the starting compound of formula II. It is preferred to use a small excess of potassium fluoride, such as an 8% to 24% excess, based on the moles of exchangeable halogen in the 2- and/or 3-position of the starting compound of formula II.

Optionally the reaction mixture may additionally contain an acid scavenger such as an alkali metal carbonate and/or a phase-transfer catalyst. The preferred alkali metal carbonate is anhydrous potassium carbonate, and the preferred phase-transfer catalysts are crown ethers and polyglycol ethers. 18-Crown-6 ether and tetraethylene glycol dimethyl ether are especially preferred. About 0.001 to 0.1% by weight of the acid scavenger and 1.0 to 40 % by weight of the phase-transfer catalyst are advantageously employed, both based on the weight of the starting compound of formula II.

Preferably the reaction temperature is in the range of 150°–240° C., most preferably in the range of 180°–240° C. Since 5-chloro-2,3-difluoropyridine boils at about 135° C., it can be advantageous to conduct the process under pressure or to allow pressure to build up during the process in order to maintain the most favorable temperature conditions. Alternatively, if one wishes to drive the reaction, for example of 2,3,5-trichloropyridine toward formation of 5-chloro-2,3-difluoropyridine of the formula I, the desired product can be removed as it is formed via a fractionating column, optionally operated under pressure. If desired, additional starting compound of the formula II can be added during the process rather than adding it all at the beginning. However, it is unnecessary to do this in order to have a high conversion of the starting 2,3,5-trihalopyridine of the formula II wherein Y is Cl or Br to a mixture of the corresponding 3,5-dihalo-2-fluoro- and 5-halo-2,3-difluoropyridines.

In one preferred method of conducting the inventive process, the starting compound of the formula II is added during the process essentially at the rate at which the product of the formula I is removed. This minimizes exposure of the starting material and the final product to high temperatures.

The reaction time is not critical and can be readily ascertained by routine experimentation. Generally the reaction time is in the range of 2 to 48 hours, preferably in the range of 12 to 24 hours. The artisan will readily appreciate that the optimum combination of time and temperature will vary with the particular system.

To carry out a reaction according to the inventive process, the solvent mixture, potassium fluoride and any optional acid scavenger or phase-transfer catalyst are preferably combined prior to the optional drying step. Then the starting compound of the formula II is added and the mixture is heated to a suitable temperature with good agitation and stirred for an appropriate length of time. The products and solvents are then recovered by distillation. Preferably 2,3,5-trichloropyridine and/or 3,5-dichloro-2-fluoropyridine is reacted in this manner with an effective amount of finely divided potassium fluoride in a polar aprotic diluent comprising a mixture of sulfolane and 5 to 30% by weight of N,N'-dimethylpropyleneurea at a temperature of from 180°–240° C., optionally in the presence of a phase-transfer catalyst.

The following non-limiting examples illustrate the reaction, of the present invention.

All temperatures are in degrees Celsius. Spray dried potassium fluoride, 99%, 1,3-dimethyl-3,4,5,6,-tetrahydro-(2H)-pyrimidinone (dimethylpropyleneurea, DMPU), 99%, tetramethylene sulfone (sulfolane), 99%, 18-crown-6-ether, 99% and tetraethylene glycol dimethyl ether, 99%, all from Aldrich Chemical Company, are used in all the examples. The 2,3,5-trichloropyridine and 2,3,5-tribromopyridine are known and are obtainable by known procedures.

Examples 1–5 illustrate typical results with the individual solvents.

EXAMPLE 1

To a 500 cc flask equipped with an efficient stirrer, a heating mantle, thermometers, a temperature controller, a distillation column packed with porcelain saddles, a water cooled condenser, a receiver and a vacuum pump is charged 79.3 g (0.43 mole) of 2,3,5-trichloropyridine (TCP), 58.4 g (1.01 mole) of potassium fluoride and 301.2 g of dimethyl-propyleneurea (DMPU). The stirred mixture is heated to 222° C. and held for 4 hours. The mixture is cooled and subjected to vacuum distillation to remove 38.9 g of liquid. The product yield is 61.0% with the composition of the mixture by glpc analysis being 21.0% 5-chloro-2,3-difluoropyridine (CDFP) and 35.7% 3,5-dichloro-2-fluoropyridine (DCFP).

EXAMPLE 2

To a 500 cc flask as described above is charged 78.4 g (0.43 mole) of TCP, 55.0 g (0.95 mole) of potassium fluoride and 300.4 g of DMPU. The stirred mixture is heated to 220° C. and held for 16 hours. The mixture is cooled and subjected to vacuum distillation to remove 31.5 g of liquid. The product yield is 59.9% with the composition of the mixture by glpc analysis being 38.3% CDFP and 21.0% DCFP.

EXAMPLE 3

To a 500 cc flask equipped as described above is charged 78.6 g (0.43 mole) of TCP, 62.0 g (1.07 mole) of potassium fluoride and 200.2 g of DMPU. The stirred mixture is heated to 180° C. and held for 24 hours. The mixture is cooled and subjected to vacuum distillation to remove 36.9 g of liquid. The product yield is 50.9% with the composition of the mixture by glpc analysis being 23.6% CDFP and 26.6% DCFP.

EXAMPLE 4

To a 500 cc flask equipped as described above is charged 79.5 g (0.44 mole) of TCP, 54.0 g (0.93 mole) of potassium fluoride and 401.5 g of sulfolane. The stirred mixture is heated to 220° C. and held for 16 hours. The mixture is cooled and subjected to vacuum distillation to remove 56.0 g of liquid. The product yield is 73.3% with the composition of the mixture by glpc analysis being 32.4% CDFP and 40.9% DCFP.

EXAMPLE 5

To a 500 cc flask equipped as described above is charged 79.4 g (0.44 mole) of TCP, 61.3 g (1.06 mole) of potassium fluoride and 403.6 g of sulfolane. The stirred mixture is heated to 180° C. and held for 12 hours. The mixture is cooled and subjected to vacuum distillation to remove 69.7 g of liquid. The product yield is 96.1% with the composition of the mixture by glpc analysis being 3.3% CDFP and 87.6% DCFP.

EXAMPLE 6

To a 500 ml flask equipped as described above is charged 79.9 g (0.44 mole) of TCP, 58.0 g (1.0 mole) of potassium fluoride, 210 g of sulfolane and 94 g of DMPU. The stirred mixture is heated to 220° C. and held for 4 hours. The mixture is cooled and subjected to vacuum distillation to remove 59.4 g of liquid. The product yield is 84% with the composition of the mixture by glpc analysis being 22.6% CDFP and 58.4% DCFP.

EXAMPLE 7

To a 500 ml flask equipped as described above is charged 83.2 g (0.46 mole) of TCP, 54.6 g (0.94 mole) of potassium fluoride, 212 g of sulfolane and 93.2 g of DMPU. The stirred mixture is heated to 220° C. and held for 16 hours. The mixture is cooled and subjected to vacuum distillation to remove 70.5 g of liquid. The product yield is 86.7% with the composition of the mixture by glpc analysis being 42.13% CDFP and 44.52% DCFP.

EXAMPLE 8

To a 500 cc flask equipped as described above is charged 79.7 g (0.44 mole) of TCP, 58.6 g (1.01 mole) of potassium fluoride, 285 g of sulfolane and 16.3 g of DMPU. The stirred mixture is heated to 220° C. and held for 4 hours. The mixture is cooled and subjected to vacuum distillation to remove 65.5 g of liquid. The product yield is 92.3% with the composition of the mixture by glpc analysis being 14.0% CDFP and 74.9% DCFP.

EXAMPLE 9

To a 500 cc flask equipped as described above is charged 79.4 g (0.44 mole) of TCP, 58.4 g (1.01 mole) of potassium fluoride, 285 g of sulfolane and 15 g of DMPU. The stirred mixture is heated to 220° C. and held for 16 hours. The mixture is cooled and subjected to vacuum distillation to remove 56.4 g of liquid. The product yield is 84.3% with the composition of the mixture by glpc analysis being 28.9% CDFP and 51.1% DCFP.

EXAMPLE 10

To a 500 cc flask equipped as described above is charged 79.0 g (0.43 mole) of TCP, 61.4 g (1.06 mole) of potassium fluoride, 5.7 g of 18-crown-6 ether (0.02 mole) and 401.5 g of DMPU. The stirred mixture is heated to 220° C. and held for 24 hours. The mixture is cooled and subjected to vacuum distillation to remove 31.8 g of liquid. The product yield is 36.4% with the composition of the mixture by glpc analysis being 23.6% CDFP and 12.8% DCFP.

EXAMPLE 11

To a 500 cc flask equipped as described above is charged 82.6 g (0.45 mole) of TCP, 55.6 g (0.96 mole) of potassium fluoride, 6.1 g (0.03 mole) of tetraethylene glycol dimethyl ether, and 300 grams of DMPU. The stirred mixture is heated to 220° C. and held for 16 hours. The mixture is cooled and subjected to vacuum distillation to remove 33.5 g of liquid. The product yield is 39.9% with the composition of the mixture by glpc analysis being 21.7% CDFP and 18.2% DCFP.

EXAMPLE 12

To a 500 cc flask equipped as described above is charged 78.9 g (0.43 mole) of TCP, 58.5 g (1.0 mole) of potassium fluoride, 6.2 g (0.03 mole) of tetraethylene glycol dimethyl ether, and 301 grams of sulfolane. The stirred mixture is heated to 220° C. and held for 16 hours. The mixture is cooled and subjected to vacuum distillation to remove 60.0 g of liquid. The product yield is 86.0% with the composition of the mixture by glpc analysis being 32.9% CDFP and 53.1% DCFP.

EXAMPLE 13

To a 500 cc flask equipped as described above is charged 79.0 g (0.43 mole) of TCP, 58.2 g (1.0 mole) of potassium fluoride, 10.4 g (0.05 mole) of tetraethylene glycol dimethyl ether, 281.7 g of sulfolane and 10.2 g of DMPU. The stirred mixture is heated to 220° C. and held for 16 hours. The reaction mixture is cooled and subjected to vacuum distillation to remove 62.0 g of liquid. The product yield is 89.0% with the composition of the mixture by glpc analysis being 36.8% CDFP and 52.2% DCFP.

EXAMPLE 14

To a 500 cc flask equipped as described above is charged 80.3 g (0.44 mole) of TCP, 58.1 g (1.0 mole) of potassium fluoride, 32.8 g (0.16 mole) of tetraethylene glycol dimethyl ether, 243.5 g of sulfolane and 32.9 g of DMPU. The stirred mixture is heated to 220° C. and held for 16 hours. The mixture is cooled and subjected to vacuum distillation to remove 57 g of liquid. The product yield is 80.8% with the composition of the mixture by glpc analysis being 34.4% CDFP and 46.4% DCFP.

EXAMPLE 15

To a 500 cc flask equipped as described above is charged 79.5 g (0.44 mole) of TCP, 58.4 g (1.01 mole) of potassium fluoride, 285 g of sulfolane and 15 g of tetramethylurea. The stirred mixture is heated to 220° C. and held for 16 hours. The mixture is cooled and subjected to vacuum distillation. The amount of CDFP and DCFP in the distillate is determined by glpc analysis.

EXAMPLE 16

To a 500 cc flask equipped as described above is charged 82.0 g (0.26 mole) of 2,3,5-tribromopyridine (TBP), 34.6 g (0.60 mole) of potassium fluoride, 280 g of sulfolane and 25 g of DMPU. The stirred mixture is heated to 220° C. and held for 16 hours. The mixture is cooled and subjected to vacuum distillation. The amount of 5-bromo-2,3-difluoropyridine (BDFP) and 3,5-dibromo-2-fluoropyridine (DBFP) in the distillate is determined by glpc analysis.

The following examples illustrate the reaction of 3,5-dichloro-2-fluoro pyridine with potassium fluoride.

EXAMPLE 17

To a 500 cc flask equipped as described above is charged 79.0 g (0.44 mole) of DCFP, 29.2 g (0.5 mole) of potassium fluoride, and 300 grams of sulfolane. The stirred mixture is heated to 220° C. and held for 16 hours. The mixture is cooled and subjected to vacuum distillation to remove 57.9 g of liquid. The fluoropyridine recovery is 68.9% with the composition of the mixture by glpc analysis being 36.5% CDFP and 31.6% unreacted DCFP.

EXAMPLE 18

To a 500 cc flask equipped as described above is charged 79.5 g (0.44 mole) of DCFP, 29.2 g (0.5 mole) of potassium fluoride, 210.4 g of sulfolane and 93.4 g of DMPU. The stirred mixture is heated to 220° C. and held for 4 hours. The mixture is cooled and subjected to vacuum distillation to remove 67.9 g of liquid. The fluoropyridine recovery is 95.8% with the composition of the mixture by glpc analysis being 16.9% CDFP and 72.9% DCFP.

EXAMPLE 19

To a 500 cc flask equipped as described above is charged 61.8 g (0.34 mole) of DCFP, 23.8 g (0.41 mole) of potassium fluoride, 212.8 g of sulfolane and 91.0 g of DMPU. The stirred mixture is heated to 220° C. and held for 16 hours. The mixture is cooled and subjected to vacuum distillation to remove 58.6 g of liquid. The fluoropyridine recovery is 98.9% with the composition of the mixture by glpc analysis being 56.8% CDFP and 31.4% DCFP.

EXAMPLE 20

To a 500 cc flask equipped as described above is charged 79.1 g (0.43 mole) of DCFP, 29.6 g (0.51 mole) of potassium fluoride, 286.6 g of sulfolane and 15.4 g of DMPU. The stirred mixture is heated to 220° C. and held for 4 hours. The mixture is cooled and subjected to vacuum distillation to remove 75.9 g of liquid. The fluoropyridine recovery is 100% with the composition of the mixture by glpc analysis being 15% CDFP and 83.2% DCFP.

EXAMPLE 21

To a 500 cc flask equipped as described above is charged 78.7 g (0.43 mole) of DCFP, 30.8 g (0.53 mole) of potassium fluoride, 280 g of sulfolane and 20 g of DMPU. The stirred mixture is heated to 220° C. and held for 16 hours. The mixture is cooled and subjected to vacuum distillation to remove 68.5 g of liquid. The fluoropyridine recovery is 95% with the composition of the mixture by glpc analysis being 31.4% CDFP and 60.3 DCFP.

EXAMPLE 22

To a 500 cc flask equipped as described above is charged 79.6 g (0.48 mole) of DCFP, 29.7 g (0.51 mole) of potassium fluoride, 10.2 g (0.05 mole) of tetraethylene glycol dimethyl ether, 280 g of sulfolane and 10.1 g of DMPU. The stirred mixture is heated to 220° C. and held for 16 hours. The mixture is cooled and subjected to vacuum distillation to remove 70.0 g of liquid. The fluoropyridine recovery is 98.3% with the composition of the mixture by glpc analysis being 28.0% CDFP and 66.4% DCFP.

The following examples illustrate the reaction of mixtures of 2,3,5-trichloropyridine and 3,5-dichloro-2-fluoro pyridine with potassium fluoride.

EXAMPLE 23

To a 500 cc flask equipped as described above is charged 41.0 g (0.21 mole) of TCP, 37.1 g (0.22 mole) of DCFP, 38.7 g (0.67 mole) of potassium fluoride, 287.5 g of sulfolane and 15.1 g of DMPU. The stirred mixture is heated to 220° C. and held for 4 hours. The mixture is cooled and subjected to vacuum distillation to remove 70.1 g of liquid. The fluoropyridine recovery is 100% with the composition of the mixture by glpc analysis being 14.9% CDFP and 79.2% DCFP.

EXAMPLE 24

To a 500 cc flask equipped as described above is charged 39.8 g (0.22 mole) of TCP, 36.2 g (0.22 mole) of DCFP, 38.0 g (0.66 mole) of potassium fluoride, 285.1 g of sulfolane and 15.3 g of DMPU. The stirred mixture is heated to 220° C. and held for 16 hours. The mixture is cooled and subjected to vacuum distillation to remove 59.4 g of liquid. The fluoropyridine recovery is 92.8% with the composition of the mixture by glpc analysis being 28.8% CDFP and 58.3% DCFP.

What is claimed is:

1. A process for the preparation of a 2,3-difluoro-5-halopyridine of the formula I

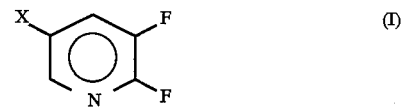

wherein X is Cl or Br, which comprises reacting a starting 2,3,5-trihalopyridine of the formula II

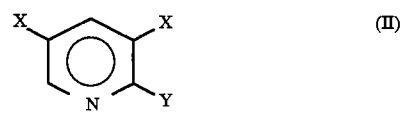

wherein each X is individually Br or Cl and Y is F, Cl or Br with an effective amount of potassium fluoride in a polar aprotic diluent comprising a mixture of sulfolane and a tetraalkylurea and/or a dialkyl-alkyleneurea, at an effective temperature of from 150° C. up to the boiling point of the diluent, optionally in the presence of an alkali metal carbonate as acid scavenger and/or a phase-transfer catalyst.

2. A process according to claim 1, wherein X and Y are both Cl.

3. A process according to claim 1, wherein the tetralkylurea is tetra-substituted by $C_1$–$C_4$ alkyl groups.

4. A process according to claim 3, wherein the tetralkylurea is tetra-substituted by methyl or ethyl groups.

5. A process according to claim 4, wherein the tetralkylurea is tetramethylurea.

6. A process according to claim 1, wherein the dialkyl-alkyleneurea is an N,N-di($C_1$–$C_2$alkyl)-N'-$C_4$–$C_5$alkyleneurea or an N,N'-di($C_1$–$C_2$alkyl)-N,N'-propyleneurea.

7. A process according to claim 1, wherein the dialkyl-alkyleneurea is an N,N'-di($C_1$-$C_2$-alkyl)-N,N'-propyleneurea.

8. A process according to claim 7, wherein the N,N'-di($C_1$-$C_2$alkyl)-N,N'-propyleneurea is N,N'-dimethylpropyleneurea.

9. A process according to claim 1, wherein the amount of tetralkylurea and/or dialkyl-alkyleneurea in the diluent mixture is from 5 to 95% by weight.

10. A process according to claim 9, wherein the amount of tetralkylurea and/or dialkyl-alkyleneurea in the diluent mixture is from 5 to 30% by weight.

11. A process according to claim 1, wherein the amount of diluent is 3–8 parts by weight per part of starting 2,3,5-trihalopyridine of the formula II.

12. A process according to claim 1, wherein substantially anhydrous and finely divided potassium fluoride is employed as the fluorinating agent.

13. A process according to claim 12, wherein an 8% to 24% excess of potassium fluoride is employed, based on the moles of exchangeable Cl or Br in the 2- and/or 3-position of the starting compound or compounds of formula II.

14. A process according to claim 1, wherein the temperature is in the range of 150°–240° C.

15. A process according to claim 14, wherein the temperature is in the range of 180°–240° C.

16. A process according to claim 1, which is carried out in the presence of an alkali metal carbonate as acid scavenger and/or a phase transfer catalyst.

17. A process according to claim 16, wherein the phase-transfer catalyst is a crown ether or a polyglycol ether.

18. A process according to claim 17, wherein the phase-transfer catalyst is 18-crown-6 ether or tetraethylene glycol dimethyl ether.

19. A process according to claim 1, wherein the starting compound of the formula II is added during the process essentially at the rate at which the product of the formula I is removed.

20. A process for the preparation of 5-chloro-2,3-difluoropyridine according to claim 1, which comprises reacting 2,3,5-trichloropyridine and/or 3,5-dichloro-2-fluoropyridine with an effective amount of finely divided potassium fluoride in a polar aprotic diluent comprising a mixture of sulfolane and 5 to 30% by weight of N,N'-dimethylpropyleneurea at a temperature of from 180°–240° C., optionally in the presence of a phase-transfer catalyst.

* * * * *